United States Patent [19]

Stoner

[11] Patent Number: 5,478,306
[45] Date of Patent: Dec. 26, 1995

[54] APPARATUS AND METHOD TO SUPPORT CARPALS TO AID IN THE PREVENTION AND TREATMENT OF CARPAL TUNNEL SYNDROME AND RELATED CONDITIONS

[76] Inventor: I. Paul Stoner, 515 S. Broad St., Lititz, Pa. 17543

[21] Appl. No.: 135,031

[22] Filed: Oct. 12, 1993

[51] Int. Cl.⁶ .............................. A61F 5/00; A41D 19/00
[52] U.S. Cl. .................... 602/20; 602/21; 2/170
[58] Field of Search .................... 128/878, 879, 128/875, 876; 602/20, 21, 22, 60, 61, 62, 63, 64, 76; 2/16, 44, 92, 170, 161 A, 312, 338

[56] References Cited

U.S. PATENT DOCUMENTS

| | | | |
|---|---|---|---|
| 3,086,529 | 4/1963 | Munz et al. | 128/327 |
| 3,256,882 | 6/1966 | Huber | 602/64 |
| 3,338,028 | 4/1967 | Freeman | 54/82 |
| 3,529,601 | 9/1970 | Kirkland | 602/75 |
| 3,710,790 | 1/1973 | Lemon | 602/64 |
| 3,789,842 | 2/1974 | Froimson | 128/165 |
| 3,942,525 | 3/1976 | Dragan | 128/165 |
| 4,048,991 | 9/1977 | Marx | 602/64 |
| 4,414,969 | 11/1983 | Heyman | 128/133 |
| 4,481,942 | 11/1984 | Duncan | 128/133 |
| 4,671,787 | 6/1987 | Widman | 604/179 |
| 4,864,698 | 9/1989 | Brame | 24/442 |
| 4,883,073 | 11/1989 | Aziz | 128/878 |
| 4,966,137 | 10/1990 | Davini | 602/21 |
| 4,991,234 | 2/1991 | Greenberg | 602/21 |
| 5,036,838 | 8/1991 | Sherman | 128/155 |
| 5,076,289 | 12/1991 | Darling | 128/877 |
| 5,082,156 | 1/1992 | Braun | 224/220 |
| 5,120,300 | 6/1992 | Shaw | 602/64 |

FOREIGN PATENT DOCUMENTS 2095559  10/1982  United Kingdom .............. 602/75

Primary Examiner—Michael A. Brown
Attorney, Agent, or Firm—Panitch Schwarze Jacobs & Nadel

[57] ABSTRACT

The present invention provides a device and method of use of the device to support the carpals which may aid in the prevention and treatment of carpal tunnel syndrome and related conditions. The device is a band which comprises a strip of flexible material about one half inch wide by one quarter inch thick which includes hook and loop type attachment means on opposite sides of its ends. The band can be fastened to itself around the carpal area of a user to provide specific support only to the carpal area of the user.

6 Claims, 1 Drawing Sheet

APPARATUS AND METHOD TO SUPPORT CARPALS TO AID IN THE PREVENTION AND TREATMENT OF CARPAL TUNNEL SYNDROME AND RELATED CONDITIONS

FIELD OF THE INVENTION

The present invention relates to a device which may be used to prevent and/or treat carpal tunnel syndrome or related conditions and, more particularly, a band to support the carpals which may aid in the prevention and treatment of carpal tunnel syndrome or related conditions, and a method that makes use of the band.

BACKGROUND OF THE INVENTION

Carpal tunnel syndrome is a nerve compression neuropathy at the point in the wrist where the nerve passes beneath the transverse carpal ligament. The carpal tunnel comprises the area of the wrist from the distal end of the forearm to the proximal end of the hand. The tunnel is formed by the anterior concavity of the carpal bones in the transverse carpal ligament. It is a small space with an approximately oval cross section. The space is almost completely occupied by tendons and the median nerve, so that any injury to the tendons, which can cause swelling, is easily further aggravated, especially given the high amount of movement of the wrist and hand.

Treatment for this syndrome is, in general, to allow the swollen structures to heal, thereby reducing the swelling. This has been accomplished by restricting movement of the hand and wrist area through the use of splints and bandages.

One such device is disclosed in Aziz U.S. Pat. No. 4,883,073. Aziz discloses a wrist support having a flexible substrate which includes integral splint elements positioned to limit wrist movement in both vertical and horizontal directions. As is readily apparent, the Aziz device extends from the proximal end of the fingers to approximately the middle of the forearm, thus providing support to the forearm, the carpals, and the hand.

Another device for treating Carpal Tunnel Syndrome is disclosed in Davini U.S. Pat. No. 4,966,137. Davini provides a splint in the form of a clamp which surrounds the forearm and is held in place by a bandage. The clamp and bandage disclosed extend from the proximal end of the hand into the forearm.

It has been determined that the support that these devices provide to the carpal area is compromised by the encroachment of these devices into areas of the hand and the forearm, beyond the carpal area of the wrist. It is believed that optimal prevention and treatment of Carpal Tunnel Syndrome and related conditions can be achieved by providing specific support only to the carpal area of the wrist, and not allowing the support device to extend into the adjacent hand and/or forearm.

SUMMARY OF THE INVENTION

Briefly stated, the present invention provides a band to support the carpals for aiding in the prevention and treatment of carpal tunnel syndrome and related conditions which comprises an elongated strip of limited stretch material having a top surface, a bottom surface, two ends, and a predetermined maximum width generally corresponding to the width of the carpal area. Attachment means are provided for attaching the two ends of the strip together, so that the band may be secured around the carpal area of a user to provide support for the carpal area. In the preferred embodiment hook and loop material is used as the attachment means on opposite sides of opposite ends of the strip. Thus, the strip can be wrapped entirely around the carpal area and then secured to itself by overlapping the hook and loop fastening components and pressing them together to form a secure connection to create a continuous secure wrapping around only the carpal area of a user.

The present invention further comprises a method for supporting the carpals for aiding in the prevention or treatment of carpal tunnel syndrome and related conditions. The first step comprises providing an elongated strip of limited stretch material, the strip of material having a first end, a second end, a top surface, a bottom surface, and a predetermined maximum. width generally corresponding to the width of the carpal area. The strip includes one complement of hook and loop fastening material on the top surface of the first end of the strip and the other complement of hook and loop material on the bottom surface of the second end of the strip.

The second step in the method comprises snugly binding the carpal area by wrapping the strip only around the carpal area and joining the strip to itself by placing the second end of the strip over the first end of the strip and fastening the hook and loop material together to form a continuous band. The band provides specific support to the carpal area of a user.

BRIEF DESCRIPTION OF THE DRAWING

The foregoing summary, as well as the following detailed description of preferred embodiments of the invention, will be better understood when read in conjunction with the appended drawing. For the purpose of illustrating the invention, there is shown in the drawing an embodiment which is presently preferred. It should be understood, however, that the invention is not limited to the precise arrangement and instrumentality shown. In the drawing.

DETAILED DESCRIPTION OF THE PREFERRED EMBODIMENT

Figure 1:
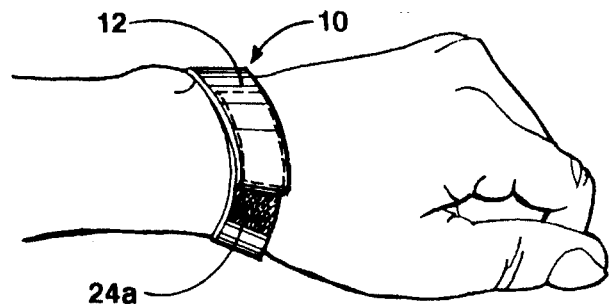
FIG. 1 is a perspective view of a band for supporting the carpals for aiding in the prevention of or treating carpal tunnel syndrome in accordance with a preferred embodiment of the present invention.
Figure 2:
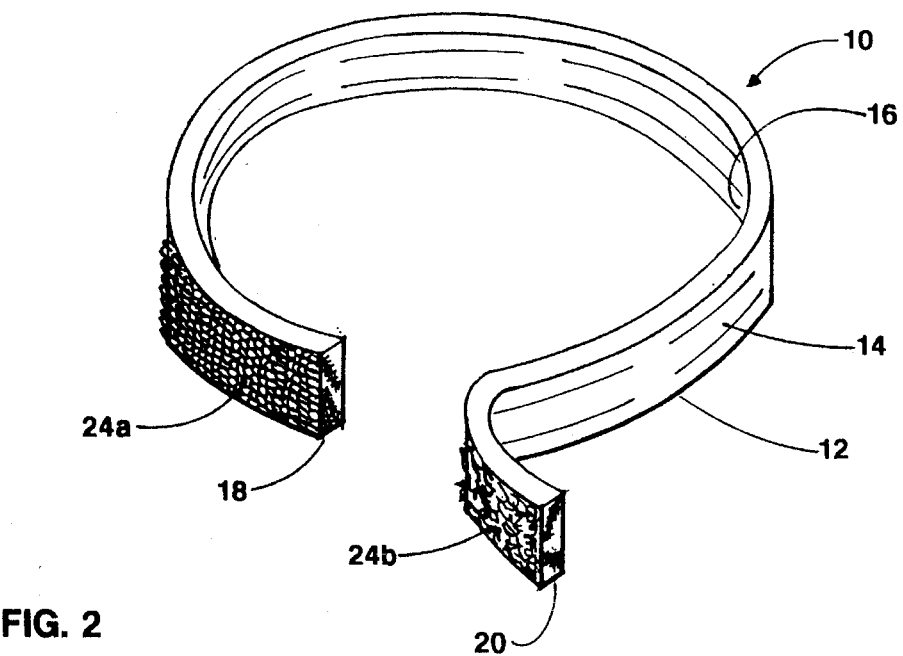
FIG. 2 is an enlarged perspective view of the band shown in FIG. 1.

Certain terminology is used in the following description for convenience only and is not limiting. The term "carpal area" is meant to only cover the portion of the wrist comprising the carpal tunnel, or that part of the arm from the proximal end of the hand to the distal end of the forearm. The term "hand" is not meant to include the wrist (carpus) and its eight bones. The term "treating" is meant to include both preventive therapy prior to the occurrence of a condition (e.g. carpal tunnel syndrome) and treatment of an existing condition. The terminology includes the words above specifically mentioned, derivatives thereof and words of similar import.

The present invention provides an improved apparatus and method for supporting the carpals which may aid in preventing and/or treating carpal tunnel syndrome and related conditions. Referring to the drawings in detail, where like numerals are used to indicate like elements throughout, FIGS. 1 through 4 show a band 10 in accordance with a presently preferred embodiment of the present invention. The band 10 is used to support the carpals and may aid in the prevention and the treatment of carpal tunnel syndrome. The band 10 comprises an elongated strip of material 12 having a top surface 14, a bottom surface 16, two ends 18, 20, and a predetermined maximum lateral width 22 generally corresponding to the width of the carpal area of a human.

Since the carpal area of a human is a relatively thin area, comprising only the part of the body from the proximal end of the hand to the distal end of the forearm, the predetermined maximum width 22 of the band 10 in most applications is approximately one-half inch. However, the width 22 of the band 10 may be less than the maximum width and may vary from user to user depending upon the width of the individual user's carpal area. By limiting the width of the band 10 in this manner, only the carpal area of the user is supported, stabilized or otherwise affected, and the forearm and/or the hand remains unfettered.

Generally, the length of the strip 12 will be at least slightly greater than the circumference of the wrist or carpal area, which is generally between seven to ten inches. Thus, a longer strip 12 may be used to treat adults or others having a carpal area of a greater circumference and a shorter strip 12 may be employed for children, or individuals having a carpal area of a smaller circumference.

Figure 4:
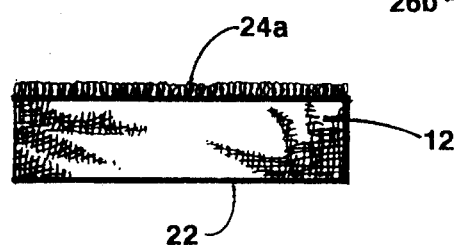
FIG. 4 is an enlarged cross-sectional view of the band shown in FIG. 1 taken along line 4—4 of FIG. 3.

The strip 12 may be constructed of any material or fabric that is generally stiff enough to at least partially stabilize and provide support for the carpal area, yet flexible enough to bend around the carpal area of the user with limited stretch when installing. For a durable band 10 which may be reused, one-quarter inch thick stitched nylon fabric is preferred. FIG. 4 is a cross-sectional view of band 10, and illustrates the thickness presently used for a stitched nylon construction in order to impart the requisite amount of stiffness to band 10. It should be noted that the thickness of the band 10 may vary depending upon the stiffness and amount of stretch inherent in the material used. Other suitable synthetic or natural materials envisioned include cotton fabric, leather, plastic, and combinations thereof.

The band 10 includes attachment means 24 for attaching the two ends 18, 20 of the strip 12 together, such that the band 10 may be snugly secured around the carpal area of a user to provide support thereof, as illustrated in FIG. 1. The preferred attachment means 24 is hook and loop material, such as that sold under the trademark VELCRO. The hook section 24a is formed with a large number of relatively small hook-like elements projecting from a base surface; the loop section 24b is formed with matted entangled fibers forming many small loops projecting from a base surface. As is known, when the hook section 24a and loop section 24b are pressed together, the hooks become entangled with the loops such that the two surfaces are held together with a relative degree of firmness, forming a secure connection having a good resistance against shear in the direction co-planar of the fastener sections. Hook section 24a and loop section 24b are easily separated from each other by peeling one section back from the other. The attachment means 24 may be affixed to the strip 12 by any known method, including sewing, gluing, etc.

Figure 3:
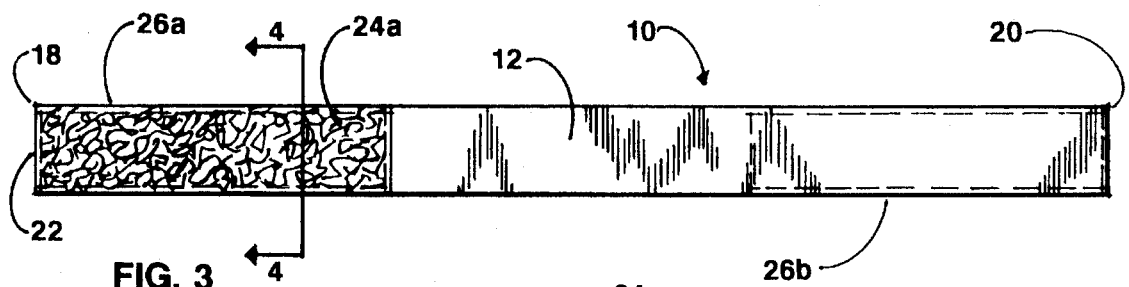
FIG. 3 is an enlarged top plan view of the band shown in FIG. 1.

FIG. 3 shows first and second mating portions of a hook and loop-type fabric fastening material positioned on opposite sides 14, 16 of opposite ends 18, 20 of strip 12. A first mating portion, in the illustrated embodiment the hook section 24a is attached to the top side 14 of one end 18 and a second mating portion, in the illustrated embodiment the loop section 24b is attached to the bottom side 16 of the other end 20. The portions of the strip 12 to which the fastening means 24a, 24b are attached comprise corresponding faces 26a, 26b. Thus, the band 10 can be attached to itself to form a continuous band around the carpal area of a user as shown in FIG. 1. Generally, each face, 26a, 26b preferably comprises about one-third of the overall length of the band. Thus, limited adjustment is provided by the length of each face 26a, 26b.

In use, support for the carpals may be provided by snugly binding the carpal area of a user by wrapping the strip 12 around the carpal area and joining the strip 12 to itself, placing end 20 over the top 14 of end 18 and pressing each of the faces 26a, 26b together, thus forming a secure attachment. The ends 18, 20 are easily separated from each other by peeling back each face 26a, 26b from the corresponding end 18. The advantage of this connection is it is easily engaged and disengaged, yet when pressed together, forms a secure connection. The band 10, thus wrapped securely around the carpal area of the user, provides specific support and stability only to the carpal area of the wrist. No extraneous additional support is imparted to the forearm or the hand of the user and differences between the dimensions of surrounding areas do not detract from the support provided by the band 10.

Other embodiments of the present invention envisioned are to provide alternate means to adjust the length of the band. This may be accomplished by providing a clamp in conjunction with a ring (not shown). Additionally, other attachment means 24, such as a hook, clamp, or buckle and tongue, for securing the strip 12 to itself may be used without departing from the spirit or scope of the present invention.

From the foregoing description, it can be seen that the present invention comprises a device and method for supporting the carpals to prevent or aid in the treatment of carpal tunnel syndrome and related conditions. It will be appreciated by those skilled in the art that changes could be made to the embodiment described above without departing from the broad inventive concepts thereof. It is understood, therefore, that this invention is not limited to the particular embodiments disclosed, but it is intended to cover all modifications within the spirit and scope of the present invention as defined by the appended claims.

What is claimed is:

1. A method of supporting a user's carpals to aid in the prevention and treatment of carpal tunnel syndrome and related conditions comprising:

providing an elongated strip of limited stretch material, said strip of material having a first end, a second end, a top surface, a bottom surface, and a predetermined maximum width generally corresponding to the width of the carpal area, said width being approximately one-half inch, the strip including one complement of hook and loop type fastening material on the top surface proximate to the first end and the other complement of hook and loop material on the bottom surface proximate to the second end;

snugly binding the carpal area by wrapping the strip only around the carpal area and joining the strip to itself by placing the second end of the strip over the first end of the strip and fastening the hook and loop material together to form a continuous band, whereby said band provides specific support to only the carpal area of a user.

2. A band for supporting a user's carpals to aid in prevention or treatment of carpal tunnel syndrome and related conditions comprising:

an elongated strip of limited stretch material having a top surface, a bottom surface, two ends, and a predetermined maximum width generally corresponding to the width of the carpal area, said width being approximately one-half inch; and attachment means for attaching the two ends of the strip together, such that the band may be snugly secured around the carpal area of a user to provide support to only the carpal area.

3. The apparatus of claim 2 wherein the attachment means comprises first and second mating portions of a hook and loop-type fabric fastening material, the first mating portion being attached to the top side of one end of the band, and the second mating portion being attached to the bottom side of the opposite end of the band such that the band can be fastened to itself around the carpal area of a user.

4. The apparatus of claim 3 wherein the band has a length between seven to ten inches and a thickness of approximately one-quarter inch, so that only the carpal area of a user is supported.

5. The apparatus of claim 2 further comprising means for adjusting the length of the band.

6. The apparatus of claim 2 wherein the material is selected from the group consisting of cotton fabric, nylon cord, leather, and plastic.

* * * * *